United States Patent
Awakowicz et al.

[11] Patent Number: 6,037,562
[45] Date of Patent: Mar. 14, 2000

[54] ARRANGEMENT AND PROCESS FOR STERILIZING CONTAINERS BY MEANS OF LOW-PRESSURE PLASMA

[75] Inventors: Peter Awakowicz, Munich; Robert Frost, Landshut, both of Germany

[73] Assignee: Ruediger Haaga GmbH, Altoberndorf, Germany

[21] Appl. No.: 09/236,564

[22] Filed: Jan. 26, 1999

[30] Foreign Application Priority Data

Feb. 17, 1998 [DE] Germany .............................. 198 06 519

[51] Int. Cl.[7] ...................................................... B23K 9/00
[52] U.S. Cl. ................................ 219/121.59; 219/121.52; 219/121.48; 422/23; 422/906; 315/111.21
[58] Field of Search .......................... 219/121.43, 121.59, 219/121.48, 121.52; 422/23, 906; 118/723 I; 315/111.21

[56] References Cited

U.S. PATENT DOCUMENTS

| | | | |
|---|---|---|---|
| 3,701,628 | 10/1972 | Ashman et al. | 422/23 |
| 5,521,351 | 5/1996 | Mahoney | 219/121.59 |
| 5,656,238 | 8/1997 | Spencer et al. | 422/23 |
| 5,801,354 | 9/1998 | Kasper . | |

*Primary Examiner*—Mark Paschall
*Attorney, Agent, or Firm*—Evenson, McKeown, Edwards & Lenahan, PLLC

[57] ABSTRACT

In order to sterilize the inner surfaces and the outer surface area located in the area of a filling opening of pressure sensitive non-electroconductive containers by means of a low-pressure plasma, an evacuable chamber is provided, which is essentially formed by two electrodes which surround the container.

34 Claims, 1 Drawing Sheet

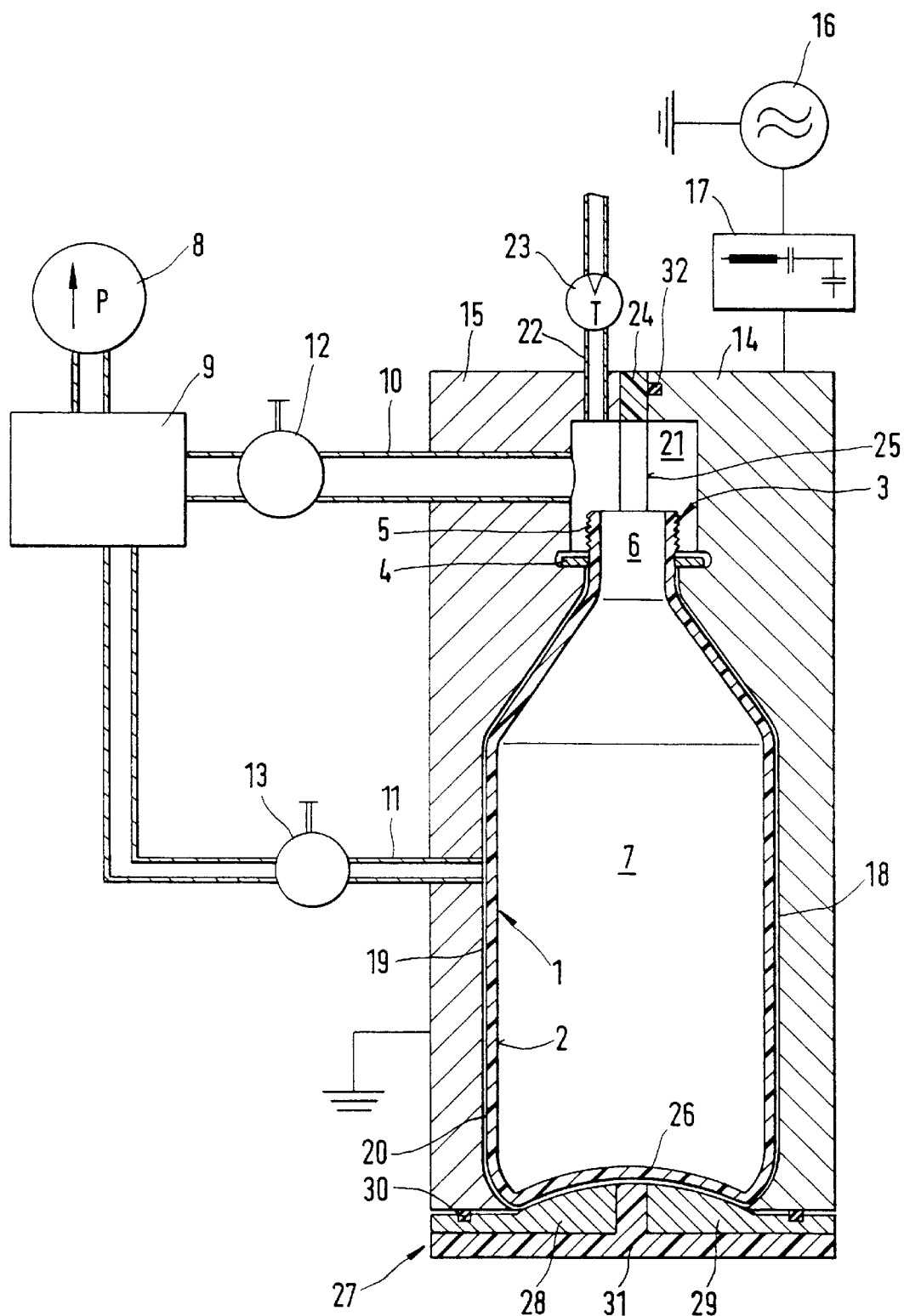

ARRANGEMENT AND PROCESS FOR STERILIZING CONTAINERS BY MEANS OF LOW-PRESSURE PLASMA

BACKGROUND AND SUMMARY OF THE INVENTION

This application claims the priority of German application 198 06 519.01, filed Feb. 17, 1998, the disclosure of which is expressly incorporated by reference herein.

The present invention relates to an arrangement for sterilizing the inner surfaces as well as an area of the outer surfaces, located at a filling opening, of pressure sensitive, non electroconductive containers by means of a low-pressure plasma, comprising an evacuable chamber for taking up the containers. The arrangement comprises a vacuum pump for evacuating the chamber, a supply pipe for supplying gas to be ionized, which pipe is connected to the chamber, two electrodes which surround the containers with shell-like areas and which electrodes generate the plasma, the electrodes having a recess in the area of the filling opening, said recess having clearance in relation to the container, and a high frequency generator for applying an alternating voltage at one of the electrodes, one of which is grounded.

In the case of an arrangement of this type (U.S. Pat. No. 5,801,354), the electrodes are arranged in the inside of the chamber, so that the area outside of the electrodes must also be evacuated. This leads on the one hand to considerable mechanical complications and on the other to increased power consumption. The known arrangement is however advantageous in that, due to the electrodes which closely surround the container, the plasma is essentially only ignited in the inside of the container, so that the outer surfaces of the container, which are not to be sterilized, are not hit by the plasma. As the vacuum prevails inside the container as well as outside it, the containers do not have to be dimensionally stable.

It is an object of the present invention, while maintaining the above mentioned advantages, to simplify the mechanical design and reduce power consumption.

This object has been achieved according to the present invention in that the electrodes also form the evacuable chamber.

As in the above prior art, the electrodes surround the container leaving a gap, which makes possible the formation of a vacuum also outside of the containers, which gap however is so narrow on the other side that no plasma can be ignited in the gap. The plasma is therefore essentially ignited only on the inside of the containers, so that only the inner surfaces of the containers, together with the outer surfaces in the area of the filling opening, are sterilized. This results in a high level of effectiveness. As a result of the electrodes themselves forming the evacuable chamber, and not being arranged in an evacuable reactor, the volume to be evacuated is reduced considerably. The space to be evacuated corresponds therefore essentially only to the inside of the containers to be sterilized, although these themselves do not form the reactor.

In preferred embodiments of the present invention it is provided that both electrodes, with the aid of an intermediary insulator, butt in a sealed manner against each other with a partition line between them.

The electrodes surround the respective container with shell-like areas, which can be moved apart for the insertion of the container into the chamber. Furthermore, the electrodes are provided with extensions which are arranged at the bottom of the container and which are insulated against each other, which extensions are arranged on a non-electroconductive supporting plate, on which the containers stand during the sterilization process. The extensions can also be separated from the shell-like areas of the electrodes.

These and further objects, features and advantages of the present invention will become more readily apparent from the following detailed description thereof when taken in conjunction with the accompanying drawing.

BRIEF DESCRIPTION OF THE DRAWING

The single drawing FIGURE is a schematic sectional view of an evacuable chamber assembly for a container to be sterilized and filled, constructed according to a preferred embodiment of the invention.

DETAILED DESCRIPTION OF THE DRAWINGS

The arrangement of the invention serves to sterilize containers 1 by means of a low-pressure plasma. In the case of these containers 1, which are pressure sensitive and non-electroconductive, it is the inner surfaces 2 in particular which need to be freed of bacteria. Of the outer surfaces 3, in contrast, only those need to be sterilized which are located in the area of a filling opening 6, namely a transport collar 4 and a screw thread 5. In the FIGURE only one container 1 is depicted, although the arrangement can be designed for a plurality of containers 1.

For the sterilization process, the container 1 is taken up in a chamber 7 which is evacuated, which chamber 7 is connected to a vacuum pump 8. By means of a vacuum container 9, the vacuum pump 8 is connected to the chamber 7 by means of two suction tubes 10 and 11. The vacuum container 9 serves as a vacuum distributor for the two suction tubes 10 and 11. A regulator valve 12 located in the suction tube 10 serves to regulate the pressure in the chamber 7 and therefore also in the container 1. The valve 13 located in the suction tube 11 has another function which will be described below and which is not needed for the actual evacuation of the chamber 7.

The vacuum container 9 permits an accelerated evacuation as well as the use of a vacuum pump 8 using less power. The vacuum pump 8 can evacuate the vacuum container 9 during the sterilization process and during the feeding of a new container 1, which vacuum container 9 for its part then evacuates the chamber 7 speedily after the valve 12 is opened.

In order to generate the plasma, two electrodes 14 and 15 are provided, of which the electrode 14 is charged with an alternating voltage and the electrode 15 is grounded. The two electrodes 14 and 15 are so formed that they form the chamber 7 during operation, which chamber 7 takes up the container 1. This permits a vacuum in the inside of the container 1 as well as outside the container 1, so that said container can be pressure sensitive. The electrodes can be so designed that they are arranged at a plurality of adjacently arranged containers 1.

A high frequency generator 16 generates the alternating voltage, which delivers a power at a permitted industrial frequency, for example 13.56 or 27.12 MHz. The power is capacitively sourced by a so-called matchbox 17 by means of the electrode 14. All other apparatus, with the exception of the high frequency generator 16, are applied to the other, grounded electrode 15.

The two electrodes 14 and 15 have shell-like areas 18 and 19, with which they surround the container 1, each one covering half of the periphery. This gives rise to a gap 20 along the outer contour of the container 1. The gap 20 should be so narrow that no plasma can be ignited therein. This requirement is fulfilled when the gap 20 measures only a few millimeters.

Although both electrodes 14 and 15 are arranged outside of the container 1, this arrangement results in the plasma being essentially only ignited in the inside of the container 1, so that essentially only the inner surfaces 2 of the container 1 are sterilized.

In addition to the inner surfaces 2, also a part of the outer surfaces 3 in the area of the filling opening 6 is sterilized, the electrodes 14 and 15 have in this area a recess 21 which permits a clearance in relation to the outer surfaces 3. The ignited plasma can thus also reach the transport collar 4 and the screw thread 5.

A supply pipe 22 for supplying the gas to be ionized enters the chamber 7. The plasma gas is let into the chamber 7, and thus into the container 1, by means of a choker valve 23. During the sterilization process, by means of gas feed and simultaneous pumping by way of the regulator valve 12, the pressure can be maintained by means of a dynamic balance of flow. Also, a certain amount of process gas can simply be fed after pumping has taken place, which results in exactly the desired pressure. The pressure can be regulated by means of a pressure gauge (not shown).

The most suitable discharging pressure depends on the type of gas and can lie in the range of 0.1 Pa to several 100 Pa. A particularly suitable plasma gas is, for example, hydrogen peroxide, but other gases can generally also be used.

The two electrodes 14 and 15, which surround the container 1, butt against each other with a partition line 25 between them. In order that both electrodes 14 and 15 are electrically insulated from one another when the chamber 7 is closed, the electrode 15 is provided with an insulator 24, which covers the entire contact surface between the two electrodes 14 and 15. In order to seal off the vacuum between the two electrodes 14 and 15, a seal 32 is provided in the other electrode 14.

When the chamber 7 is closed, the container 1 stands with its bottom 26 on a reactor bottom 27, which comprises a non-electroconductive supporting plate 31 as well as two metal extensions 28 and 29 of the electrodes 14 and 15. An insulating extension of the supporting plate 31 is located between the two extensions 28 and 29. The reactor bottom 27 is sealed by means of a sealing ring 30 against the shell-like areas 18 and 19 of the electrodes 14 and 15.

Like the shell-like areas 18 and 19, the reactor bottom 27 is also formed according to the contour of the bottom 26 of the container 1. As the gap located there is also evacuated, the wall of the container 1 is not affected by a resultant force.

The sterilization process begins with the container 1 being inserted into the grounded electrode 15 by means of a feeding device (not shown) which seizes the container 1 at its transport collar 4. The chamber 7 is closed in three stages: in the first stage, the fed container 1 is sucked, by means of the suction tube 11 regulated by the valve 13 onto the electrode 15. The feeding device is then moved away. In a second stage, the electrode 14 is moved towards the electrode 15. In a last stage, the reactor bottom 27 is advanced from below. Thereafter the valve 13 is closed.

Evacuation thus takes place by means of the upper suction tube 10, which enters into the chamber 7 in the area of the recess 21. The supply pipe 22 for the gas to be ionized also enters the recess 21.

This arrangement has the advantage that the electrodes 14 and 15 themselves do not need to be arranged in a reactor, that is that the electrodes 14 and 15 do not need to be exposed on their outer surfaces to the low pressure, whereby energy consumption is significantly reduced. Furthermore the mechanical design is less complicated than in the described prior art.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An arrangement for sterilizing inner surfaces as well as an area of outer surfaces, located at a filling opening, of pressure sensitive, non-electroconductive containers by means of a low-pressure plasma, comprising:

an evacuable chamber for taking up the containers, a vacuum pump for evacuating the chamber, a supply pipe for supplying gas to be ionized, which pipe is connected to the chamber, two electrodes which surround the containers with shell-like areas, said electrodes generating the plasma, the electrodes having a recess in the area of the filling opening, said recess having clearance in relation to the container, and a high frequency generator for applying an alternating voltage at one of the electrodes, one of which is grounded, wherein the electrodes form the evacuable chamber in such a manner that surfaces of the electrodes facing away from a container being sterilized need not be evacuated.

2. An arrangement according to claim 1, wherein the electrodes, with the aid of an intermediary insulator, butt against one another in a sealed manner with partition lines between them.

3. An arrangement according to claim 1, wherein the electrodes are provided with extensions arranged at the bottom of the container and insulated against one another.

4. An arrangement according to claim 2, wherein the electrodes are provided with extensions arranged at the bottom of the container and insulated against one another.

5. An arrangement according to claim 3, wherein the extensions can be separated from the shell-like areas of the electrodes.

6. An arrangement according to claim 4, wherein the extensions are arranged on a non-electroconductive supporting plate.

7. An arrangement according to claim 4, wherein the extensions can be separated from the shell-like areas of the electrodes.

8. An arrangement according to claim 7, wherein the extensions are arranged on a non-electroconductive supporting plate.

9. An arrangement according to claim 1, wherein the shell-like areas of the electrodes can be moved away from each other.

10. An arrangement according to claim 2, wherein the shell-like areas of the electrodes can be moved away from each other.

11. An arrangement according to claim 3, wherein the shell-like areas of the electrodes can be moved away from each other.

12. An arrangement according to claim 5, wherein the shell-like areas of the electrodes can be moved away from each other.

13. An arrangement according to claim 6, wherein the shell-like areas of the electrodes can be moved away from each other.

14. A container sterilizing system comprising:

shell shaped electrodes with internal contours adapted to closely surround a hollow container and thereby form an evacuable chamber for the container, evacuating means for evacuating the chamber, gas supply means for supplying gas to be ionized to the chamber including interior spaces of the container, and high frequency generator means for applying voltage to one of said electrodes to thereby ionize the gas and sterilize the inside of the container, wherein said shell shaped electrodes are configured so as to be spaced from exterior container walls by a gap so narrow that no plasma is ignited therein during application of said voltage, and wherein said shell shaped electrodes are configured in such a manner that surfaces of the electrodes facing away from a container being sterilized need not be evacuated, and wherein the evacuating means for evacuating the chamber operably evacuates the chamber without evacuating areas outside said surfaces of the electrodes facing away from the container.

15. A container sterilizing system according to claim 14, wherein said electrodes include a recessed area which in use surrounds a filling opening of the container so that exterior surfaces of the container at the filling opening are sterilized by the ionized gas.

16. A container sterilizing system according to claim 14, wherein the electrodes, with the aid of an intermediary insulator, butt against one another in a sealed manner with partition lines between them.

17. A container sterilizing system according to claim 14, wherein the electrodes are provided with extensions arranged at the bottom of the container and insulated against one another.

18. A container sterilizing system according to claim 17, wherein the extensions can be separated from the shell-like areas of the electrodes.

19. A container sterilizing system according to claim 18, wherein the extensions are arranged on a non-electroconductive supporting plate.

20. A container sterilizing system according to claim 14, comprising means for moving the electrodes relative to one another to facilitate insertion and removal of the container.

21. A container sterilizing system according to claim 14, comprising suction means for holding a container at one of the electrodes.

22. A method of sterilizing hollow containers comprising:

surrounding a container by shell shaped electrodes with internal contours forming a chamber and adapted to closely surround a portion of a circumference of the container;

evacuating the chamber, supplying gas to be ionized to the chamber, including interior spaces of the container, and applying high frequency voltage to one of the electrodes to thereby ionize the gas and sterilize the inside of the container, wherein said shell shaped electrodes are configured so as to be spaced from exterior container walls by a gap so narrow that no plasma is ignited therein during application of said voltage, and wherein said shell shaped electrodes are configured in such a manner that said evacuating the chamber does not evacuate areas surrounding surfaces of the electrodes which face away from the container.

23. A method according to claim 22, wherein said electrodes include a recessed area which in use surrounds a filling opening of the container so that exterior surfaces of the container at the filling opening are sterilized by the ionized gas.

24. A method according to claim 22, wherein said surrounding the container includes:

sucking the container against one of the electrodes, and subsequently moving the electrodes toward one another to enclose the container and form the chamber.

25. An arrangement for sterilizing inner surfaces as well as an area of outer surfaces, located at a filling opening, of pressure sensitive, non-electroconductive containers by means of a low-pressure plasma, comprising:

an evacuable chamber for taking up the containers, a vacuum pump for evacuating the chamber, a supply pipe for supplying gas to be ionized, which pipe is connected to the chamber, two electrodes which surround the containers with shell-like areas, said electrodes generating the plasma, the electrodes having a recess in the area of the filling opening, said recess having clearance in relation to the container, and a high frequency generator for applying an alternating voltage at one of the electrodes, one of which is grounded, wherein the electrodes form the evacuable chamber, and wherein the electrodes are provided with extensions arranged at the bottom of the container and insulated against one another.

26. An arrangement according to claim 25, wherein the electrodes, with the aid of an intermediary insulator, butt against one another in a sealed manner with partition lines between them.

27. An arrangement according to claim 25, wherein the extensions can be separated from the shell-like areas of the electrodes.

28. An arrangement according to claim 25, wherein the extensions are arranged on a non-electroconductive supporting plate.

29. An arrangement according to claim 28, wherein the extensions can be separated from the shell-like areas of the electrodes.

30. An arrangement according to claim 29, wherein the shell-like areas of the electrodes can be moved away from each other.

31. A container sterilizing system comprising:

shell shaped electrodes with internal contours adapted to closely surround a hollow container and thereby form an evacuable chamber for the container, evacuating means for evacuating the chamber, gas supply means for supplying gas to be ionized to the chamber including interior spaces of the container, and high frequency generator means for applying voltage to one of said electrodes to thereby ionize the gas and sterilize the inside of the container, wherein said shell shaped electrodes are configured so as to be spaced from exterior container walls by a gap so narrow that no plasma is ignited therein during application of said voltage, and wherein the electrodes are provided with extensions arranged at the bottom of the container and insulated against one another.

32. A method according to claim 31, wherein the extensions can be separated from the shell-like areas of the electrodes.

33. A method according to claim 32, wherein the extensions are arranged on a non-electroconductive supporting plate.

34. An arrangement for sterilizing inner surfaces as well as an area of outer surfaces, located at a filling opening, of pressure sensitive, non-electroconductive containers by means of a low-pressure plasma, comprising:

an evacuable chamber for taking up the containers, a vacuum pump for evacuating the chamber, a supply pipe for supplying gas to be ionized, which pipe is connected to the chamber, two electrodes which surround the containers with shell-like areas, said electrodes generating the plasma, the electrodes having a recess in the area of the filling opening, said recess having clearance in relation to the container, and a high frequency generator for applying an alternating voltage at one of the electrodes, one of which is grounded, wherein the electrodes form the evacuable chamber, and wherein the electrodes, with the aid of an intermediary insulator, butt against one another in a sealed manner with partition lines between them.

\* \* \* \* \*